Figure 1:
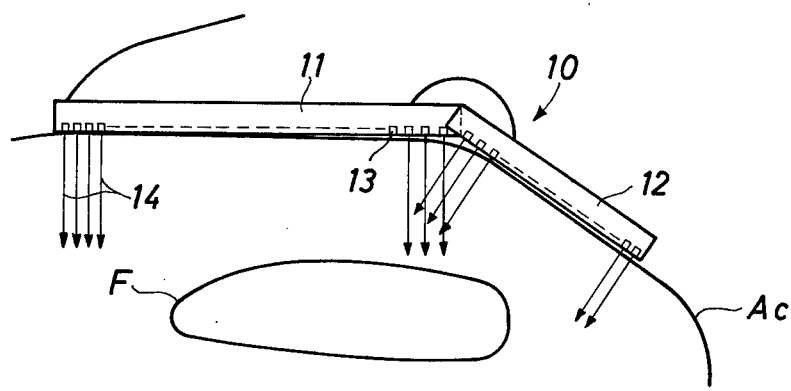

United States Patent
Lund et al.

[11] 4,030,343
[45] June 21, 1977

[54] APPARATUS FOR PROVIDING AN ULTRASONIC SECTIONAL VIEW STATING THE PROPORTION OF MEAT AND LARD IN BIOLOGICAL MATERIAL

[75] Inventors: Svend Aage Lund, Birkerod; Allan Northeved, Bagsvaerd; Poul Solfjeld, Vanlose; Knud Christian Claus Fabrin, Farum, all of Denmark

[73] Assignee: Akademiet for de tekniske Videnskaber, Svejsecentralen, Glostrup, Denmark

[22] Filed: Nov. 19, 1975

[21] Appl. No.: 633,311

[30] Foreign Application Priority Data
Nov. 19, 1974 Denmark .......................... 6011/74

[52] U.S. Cl. ........................................... 73/67.8 S
[51] Int. Cl.² ......................................... G01N 29/04
[58] Field of Search .......... 73/67.7, 67.8 R, 67.8 S, 73/67.9; 340/5 MP

[56] References Cited
UNITED STATES PATENTS
3,722,263  3/1973  Hautaniemi et al. ............ 73/67.8 S FOREIGN PATENTS OR APPLICATIONS
1,340,990  9/1962  France .......................... 73/67.8 S Primary Examiner—Richard C. Queisser
Assistant Examiner—John P. Beauchamp
Attorney, Agent, or Firm—Ladas, Parry, Von Gehr, Goldsmith & Deschamps

[57] ABSTRACT

An apparatus for providing an ultrasonic sectional view stating the proportion of meat and lard in biological material. The apparatus comprises a transducer unit and an ultrasonic pulse generator providing a periodically scanning window. Said transducer unit comprises at least two multi-crystal units, the longitudinal axes of which may form a variable angle. The joint between the multi-crystal units comprises an angle information unit. By means of said angle information unit and the means for visualizing reflected ultrasonic echoes it is possible to visualize marginal surfaces.

4 Claims, 4 Drawing Figures

APPARATUS FOR PROVIDING AN ULTRASONIC SECTIONAL VIEW STATING THE PROPORTION OF MEAT AND LARD IN BIOLOGICAL MATERIAL

The invention relates to an apparatus for providing an ultrasonic sectional view stating the proportion of meat and lard in biological material, said apparatus comprising a transducer unit of the multi-crystal type, electronic switching units, a pulse generator, and an ultrasonic pulse generator providing a periodically scanning ultrasonic window, and means for visualizing reflected ultrasonic echoes on an oscilloscope screen.

It is known to measure the depth of the meat and lard layers on animals by means of ultrasound. A transducer unit is for instance known comprising a plurality of aligned piezoelectric crystal elements. The crystal elements are separately and successively activated by means of a control circuit comprising a pulse generator controlling two electronic switching units and an ultrasonic pulse generator, whereby the first switching unit successively transmits the ultrasonic pulses to each crystal element, and the second switching unit transmits the echo pulses received from each activated crystal element to a display unit. Thus, a scanning ultrasonic window through which ultrasonic pulses are emitted and echo pulses are received is formed. In the prior art said display unit is an intensity or z-amplifier. The pulse generator also controls a step generator connected to the vertical deflection circuit of the oscilloscope and to the time base of the oscilloscope.

Said known apparatus performs a scanning at one level and permits a reflection of the received echo information to appear on the oscilloscope screen, said echo information deriving from the tissue interfaces being met by the ultrasonic beams. Said tissue interfaces may for instance be the interfaces between meat and lard. It is, however, important to note that each crystal element can only receive echo pulses returning by the same path as the transmitted ultrasonic energy, i.e. the reflecting interface between two types of biological tissue must be substantially perpendicular to the direction of transmission of the crystal element in question. This limits the scope of application of the known apparatus as it is not possible by means of said apparatus to provide an acceptable ultrasonic view of the marginal surfaces of the meat and lard layers examined, i.e. the surfaces at the edge of a meat or lard layer, because these surfaces are inclined relative to the direction of the transmitted ultrasonic energy.

The object of the invention is to provide an apparatus rendering it possible to visualize also the said marginal surfaces, the transducer unit of said apparatus comprising at least two multi-crystal units being joined or assembled in such manner that the longitudinal axes of the units form a variable angle, the joint between the multi-crystal units comprising an angle information unit for generating a voltage proportional to the angle between the multi-crystal units, said angle information unit and the means for visualizing reflected ultrasonic echoes being connected to an analog calculating circuit and to a gate circuit transmitting the angle information to the oscilloscope at a suitable moment or at suitable moments during the cycle period of the horizontal deflection or x-sweep of the oscilliscope.

The configuration, following a not straight line, of the transducer unit according to the invention makes it possible also for the marginal surfaces of the meat or lard layer to be met by perpendicularly incident, ultrasonic pulses, thus permitting said surfaces to be clearly visualized on the oscilloscope screen.

Figure 2:
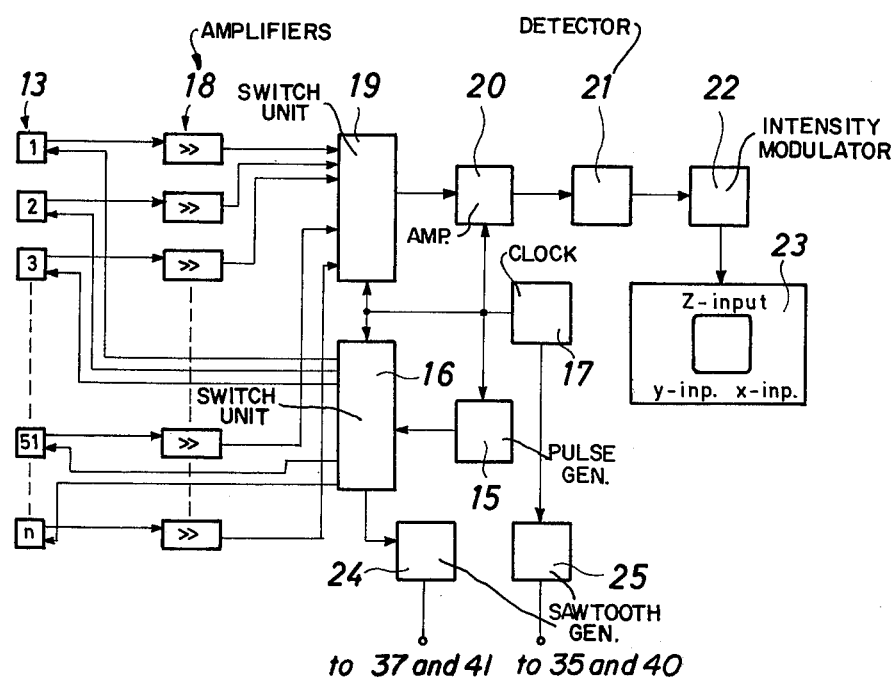
Figure 3:
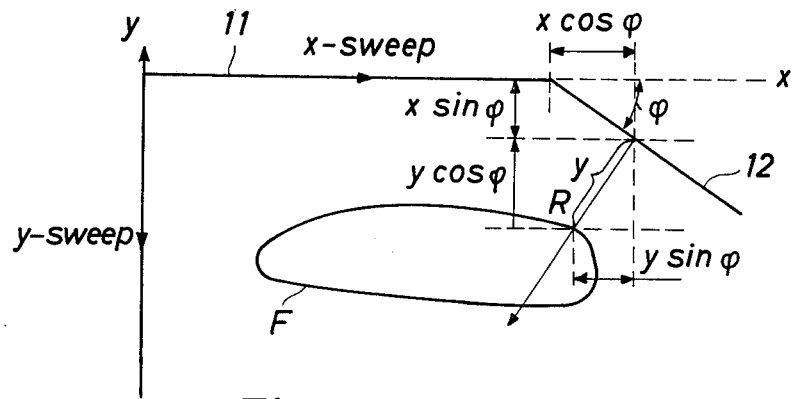
Figure 4:
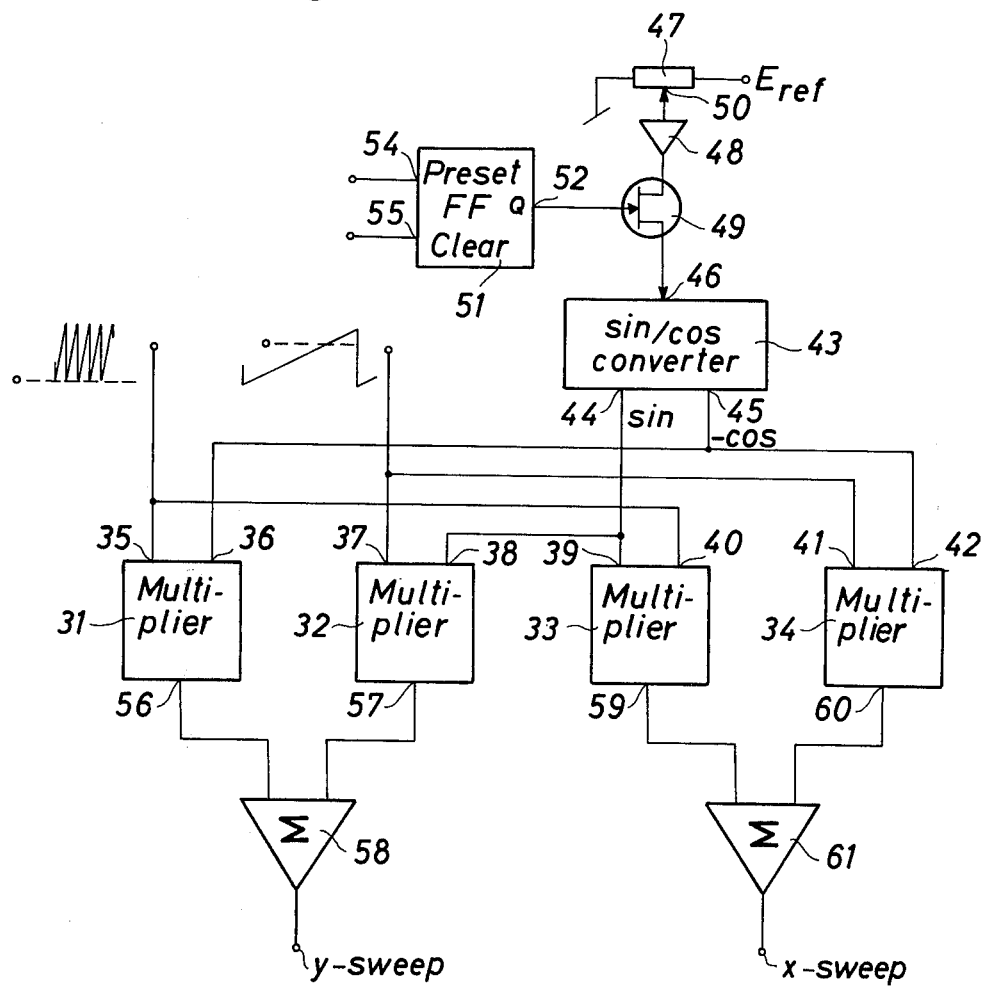

The invention will be described below with reference to the accompanying drawings, in which FIG. 1 shows a transducer unit according to the invention arranged on the outside of an animal, FIG. 2 shows a block diagram of a control circuit illustrating the control of each piezoelectric crystal element of the transducer unit, FIG. 3 shows the geometry between the joined multi-crystal elements, and FIG. 4 shows a block diagram of an analog calculating circuit to be used in the transducer unit.

FIG. 1 shows a transducer unit 10 according to the invention arranged on the outside of an animal A, the outline of which is indicated by a curve $A_c$. The meat or lard layer, the depth of which is to measured, is indicated diagrammatically by a closed curve F.

The transducer unit 10 according to the invention consists of two multi-crystal units 11 and 12 being joined in such manner that their longitudinal axes may form a variable angle $\phi$.

Each multi-crystal unit comprises a plurality of piezoelectric crystal elements 13, only roughly shown on the drawing since the periodical "Circulation" of November, 1973, pages 1069–1070 discloses the construction of such a multi-crystal unit.

The transmitting direction of each unit is indicated by lines 14, and in view of the rules of reflection for transmitted ultrasonic energy, it is obviously very difficult, if not impossible, to obtain a sufficiently clear definition of the interface between two different types of biological tissue at the end of a layer of meat or lard by means of only one multi-crystal unit 11 when operating with just one scanning direction. Such a surface, which is difficult to define, is indicated by a thick line on the curve F in FIG. 1.

The transducer unit according to the invention, comprising at least two multi-crystal units, which may form different angles, makes it possible to obtain ultrasonic echoes strong enough to visualize also such surfaces.

A transducer unit comprising only one multi-crystal unit and consequently only one scanning direction presents no problems regarding the control of the x- and the y-deflections of the oscilloscope, as it is for instance known to control the y-deflection by means of a step generator, the number of steps of which corresponds to the number of crystal elements, whereas the x-deflection is controlled by a usual sawtooth generator generating a sawtooth voltage having a gradient proportional to the velocity of sound in the tissue examined.

It is, however, not very simple to transmit angle information to the oscilloscope when the transducer unit according to the invention comprises two multi-crystal units.

An article in the "Bio-Medical Engineering" of November, 1971 discloses the control of each crystal element. Consequently, the control will here be mentioned only to the extent necessary for the understanding of the invention, cf. FIG. 2.

A plurality of crystal elements, generally indicated by 13, are numbered consecutively from 1 to $n$. In principle $n$ may be very large, but must have an upper limit if an ultrasonic view almost free of flicker is to be obtained on an oscilloscope screen. In a preferred embodiment of the transducer unit according to the invention the first multi-crystal unit 11 comprises 50 elements and the second multi-crystal unit 12 comprises 25 crystal elements. This results in a handy unit being capable of scanning a large section at a time. Therefore, the first crystal element in the second multi-crystal unit 12 is No. 51 in the range and is shown separately on the drawings.

Each crystal element receives ultrasonic energy from an ultrasonic pulse generator 15 via a first electronic switching unit 16. The main component of said switching unit may for instance comprise a shift register with 75 steps and an output for each location. Thus each crystal element 13 may successively receive a pulse from the ultrasonic pulse generator 15 and transmit a brief ultrasonic pulse in the direction 14, cf. FIG. 1. The switching unit 16 and the pulse generator 15 are controlled by a pulse generator 17. Further, it is known to activate the crystal elements 13 in such manner that e.g. the 13th, 14th and 15th elements are active during a certain time interval and the 14th, 15th and 16th elements are active during the subsequent time interval, and so on, whereby an ultrasonic window in effect, through which ultrasonic energy is emitted and received moves down through the range of crystal elements, first through the unit 11 and then through the unit 12.

The crystal elements 13 are each connected to their respective inputs in a second switching unit 19 via a separate pre-amplifier 18. Said switching unit 19 may be constructed in the same way as the first switching unit 16 and is also controlled by the pulse generator 17.

The ultrasonic echo received by each crystal element is re-converted into an electric signal being amplified in the pre-amplifier 18 and transmitted via the second switching unit 19 to an amplifier 20 time-controlled by the pulse generator 17 so that the gain of the amplifier increases as the depth from which an echo is received increases. From said amplifier 20 the signal is transmitted via a detector 21 to an intensity modulator 22, the output of which is connected to the z-input of an oscilloscope. In the oscilloscope the electronic beam is intensity-modulated by the ultrasonic echoes received appearing on the oscilloscope screen as luminous spots. The horizontal and vertical deflections of the electronic beam are controlled by a first sawtooth generator 24 and a second sawtooth generator 25, respectively. The first sawtooth generator or x-sweep generator 24 thus controls the x-deflection of the oscilloscope, and is itself controlled by the first electronic switching unit 16, the sawtooth generator being reset each time the switching unit initiates a new scanning cycle.

The second sawtooth generator or y-sweep generator 25 controls the y-deflection of the oscilloscope, and is itself controlled by the pulse generator 17, the y-sweep generator being reset each time a pulse is transmitted, said pulse initiating a new scanning period involving one crystal element.

The gradient of the sawtooth voltage produced by the y-sweep generator is proportional to the average velocity of sound transmission of the ultrasonic energy in the examined muscular and fatty tissues. Furthermore, the sweep velocities of the two sawtooth generators are mutually adjusted in such manner that each x-sweep contains as many y-sweeps as prescribed by the number of crystal elements 13, i.e. in this case 75 y-sweeps.

The angle between the two multi-crystal units 11 and 12 necessitates, however, the insertion of a particular, analog calculating circuit between the x-sweep generator 24 and the y-sweep generator 25 and between the x and the y-inputs of the oscilloscope. But before describing said calculating circuit, reference is made to FIG. 3 showing the geometry between the two multi-crystal units 11 and 12. The longitudinal axes of said units form an angle $\phi$. FIG. 3 also illustrates the sweep conditions on the oscilloscope screen. The first multi-crystal unit 11 is for instance arranged in the direction of the x-sweep, whereby the ultrasonic energy is transmitted in the negative direction of the y-sweep. The second multi-crystal unit 12 forms an angle $\phi$ with the direction of the x-sweep, whereby the ultrasonic energy is transmitted from said unit in a direction forming the angle $\phi$ with the negative direction of the y-sweep.

A reflection point R on the closed curve F of FIG. 1 illustrates that the x- and the y-sweeps of the first multi-crystal unit 11 are provided in the usual way, whereas the x- and the y-sweeps of the second multi-crystal unit 12 must be adjusted due to the introduced angle $\phi$.

Since the y-sweep generator sweeps at a constant velocity the y-coordinate of the point R must be illustrated by the term $y \cdot \cosine \phi + x \cdot \sine \phi$ in this phase of sound transmission, both terms being considered negative. Consequently, the x-coordinate of the point R of the x-sweep must be illustrated by the term $x \cdot \cosine \phi + y \cdot \sine \phi$, the first term being considered positive and the second term negative.

The above equations are, however, only valid if the origin of the x corresponds to the joint of the two multi-crystal units. This detail has, however, been considered when constructing the sawtooth generator of the x-sweep, since a part of the sawtooth voltage, i.e. the part being related to the first multi-crystal unit 11, is negative, whereas the remaining part of the sawtooth voltage, i.e. the voltage being related to the second multi-crystal unit 12, is positive. When the sawtooth voltage of the x-generator reaches two thirds of the maximum voltage, i.e. the moment when the crystal element No. 51 is activated, it assumes the value of 0 volt.

The above analogous calculating circuit is shown in FIG. 4. Four 2-input multipliers, i.e. a first multiplier 31, a second multiplier 32, a third multiplier 33, and a fourth multiplier 34 form the nucleus of said calculating circuit.

The output of the y-sweep generator 25 is parallelly connected to the first input 35 of the first multiplier 31 and the second input 40 of the third multiplier 33. The output of the x-sweep generator 24 is parallelly connected to the first inlet 37 of the second multiplier 32 and the first input 41 of the fourth multiplier 34. The remaining multiplier inputs are connected to the output side of an electronic sine-cosine converter 43, the sine-output 44 of said converter being parallelly connected to the second input 38 of the second multiplier 32 and the first input 39 of the third multiplier 33. The cosine-output 45 of the converter is parallelly connected to the second input 36 of the first multiplier 31 and the second input 42 of the fourth multiplier 34.

The sine-cosine converter 43 is an electronic circuit of known type comprising one input and two outlets, said output supplying output voltages proportional to sine for the input voltage and to cosine for the input voltage, respectively.

The input 46 of the sine-cosine converter is connected to a linear rotary potentiometer 47 via a high-impedance amplifier 48 of small amplification and to a field-effect transistor 49 working as an on-off switching unit.

The rotary potentiometer 47 is mounted at the rotating connection of the multi-crystal units. A constant reference DC voltage $E_{ref.}$ is applied on the fixed terminals of said rotary potentiometer 47, and the contact arm 50 of said rotary potentiometer 47 senses a voltage proportional to the angle $\phi$ between the longitudinal axes of the multi-crystal units 11 and 12. The angle information is, however, only to be transmitted to the oscilloscope during the part of the scanning cycle involving the second multi-crystal unit 12.

A flip-flop 51 controls the field-effect transistor 49, the Q-output 52 of said flip-flop 51 being connected to the gate 53 of said field-effect transistor 49. The preset-input 54 of the flip-flop is connected to the 51st location of the first shift register or switching unit 16 in such manner that the flip-flop is set simultaneously with the 51st crystal element in the range or the first crystal element in the second multi-crystal unit 12 being opened by a pulse. During this operation the Q-output 52 of the flip-flop assumes a voltage level corresponding to 1, the field-effect transistor 49 thus being brought into the on-position, so that the angle information from the contact arm 50 of the rotary potentiometer 47 can be transmitted to the input 46 of the sine-cosine converter. Furthermore, the clear-input 55 of the flip-flop is connected to the first location in the shift register or to the switching unit 16 in such manner that the flip-flop is reset at the beginning of a new scanning cycle. Thus the Q-output 52 is brought into the O-position and the field-effect transistor 49 is brought into the off-position, the sine-cosine converter thus receiving no signal on its input.

Finally, the outputs 56 and 57 of the first and the second multiplier, respectively, are connected to the input of a first adding operational amplifier or adder 58, whereas the outputs 59 and 60 of the third and the fourth multiplier, respectively, are connected to the input of a second adding operational amplifier or adder 61. The output of the first adder 58 is connected directly to the y-input of the oscilloscope 23, and the output of the second adder 61 is connected directly to the x-input of said oscilloscope.

In the part of the scanning cycle, where the flip-flop is set and consequently the field-effect transistor is in the on-position, the sine-cosine converter supplies voltages proportional to the sine $\phi$ and the cosine $\phi$, said cosine output of the converter being inverting. The y-sweep generator supplies a positive sawtooth voltage, whereas the sawtooth voltage supplied by the x-sweep generator is only positive as to the last third of the sawtooth voltage.

A positive voltage proportional to y appears on the input 35 of the first multiplier 31 and a negative voltage proportional to the cosine $\phi$ on the input 36 of said first multiplier 31, said voltages causing a voltage proportional to the product y cosine $\phi$ on the output 56. Thus the voltage forming the first term in the y-component is negative.

In the same way voltages proportional to the x and the sine, respectively, appear on the inputs 37 and 38 of the second multiplier 32 and the voltage x in this part of the scanning cycle being positive, the voltage of the output 57 is proportional to the product x sine $\phi$. Said voltage forming the second term in the y-component is negative, for which reason the output 57 is made inverting. The adding signal y·cosine $\phi$ + x·sine $\phi$ of the output of the first adder 58 will consequently have the correct sign.

The input of the third multiplier 33 supplies voltages proportional to the sine $\phi$ and the y, respectively, thus supplying the output 59 with a voltage proportional to the product y sine $\phi$. The output 59 is made inverting, since the above voltage forming the first term in the x-component is negative.

The inputs of the fourth multiplier 33 receive voltages proportional to the x and the cosine $\phi$, respectively, thus supplying the output 60 with a voltage proportional to the product $-x$·cosine $\phi$. The output 60 is made inverting, since the above voltage forming the second term in the x-component is positive.

The output of the second adder 61 will have the adding signal y sine $\phi$ + x cosine $\phi$, the first term being negative and the second term being positive.

In the first part of the scanning cycle, in which the flip-flop is reset and consequently the field-effect transistor is in the off-position, the potentiometer applied no signal on the sine-cosine converter, which is considered by the converter as if the angle $\phi$ were 0. Consequently, a voltage is generated on the sine-output 44, said voltage being proportional to the term sine $\phi$ = sine 0 = 0, and a voltage is generated on the cosine-output, said voltage being proportional to the term $-$cosine $\phi$ = $-$cosine 0 = $-1$. This implies that the voltages on the multiplier outputs 56 and 57 are proportional to y ($-$cosine 0) = y($-1$) = $-y$ and $-x$.sine0 = $-x$.0 = 0, respectively, i.e. the output voltage of the adder 58 is proportional to y only. The voltages of the multiplier outlets 59 and 60 are proportional to $-y$·sine0 = $-y$.0 = 0 and $-x$($-$cosine0) = $x$($-1$) = $x$, respectively, i.e. the output voltage of the adder 61 is proportional to x only.

It has already been mentioned that information concerning the angle $\phi$ is provided by means of a rotary potentiometer, the fixed terminals of which are supplied with a reference DC voltage, and the contact arm of which senses a voltage proportional to the angle $\phi$. According to the invention said angle information may also be provided by means of a strain gauge due to the fact that a larger or smaller angle $\phi$ would cause larger or smaller resistance change of the transmitter. A Wheatstone bridge registers said resistance change as an unbalance, and the generated error signal $\Delta V$ might, following a suitable amplification, be used directly as an inlet signal for the sine-cosine converter.

The above description should only be considered an illustrating example of the idea of the invention, as the apparatus in question may, of course, be modified in many, and to a person skilled in the art, obvious ways without deviating from the scope of the invention. The number of crystal elements may for instance be varied relative both to the total amount and the proportion of elements on the two multi-crystal units.

Furthermore, the x and the y-sweep generators might be interchanged.

Finally, the transducer unit might be divided into more than two mutually rotatable multi-crystal units surrounding the whole animal. In this case the analog calculation circuit (FIG. 4) might have a multiple x circuit for successively scanning the rotary potentiometers and strain gauges involved.

We claim:

1. An apparatus for carrying out an ultrasonic inspection of a body comprising:
an oscilloscope having a screen, an intensity modulation input, and first and second deflection signal inputs to which electrical signals can be applied to cause the oscilloscope's electron beam to scan the screen in mutually perpendicular directions;

a first linear array of electro-acoustic transducers arranged to emit and receive ultrasonic energy in directions parallel to a first axis;

a second linear array of electro-acoustic transducers arranged to emit and receive ultrasonic energy in directions parallel to a second axis;

an angle information unit for generating an electrical signal dependent on the angle of inclination of the first axis with respect to the second axis;

a pulse generator for generating a train of electrical pulses at a predetermined frequency;

switching means connected to the pulse generator for activating the transducers of the first and second arrays in turn whereby the transducers are successively enabled to emit pulses of ultrasonic energy and are successively rendered receptive to echoes of ultrasonic energy; and means for displaying ultrasonic echoes received successively by the transducers on the oscilloscope screen, which means comprise means connecting the transducers to the intensity modulation input of the oscilloscope to cause the electron beam of the oscilloscope to increase in intensity when an ultrasonic echo is received by a transducer which is activated by the switching means, a first sweep generator connected to the pulse generator for generating a first sweep signal at said predetermined frequency, a second sweep generator connected to the switching means for generating a second sweep signal at a frequency equal to said predetermined frequency divided by the total number of transducers in said first and second arrays, an analog calculating circuit connected between the first and second sweep generators and the first and second deflection signal inputs of the oscilloscope and a gate circuit connected between the angle information unit and the analog calculating circuit for transmitting the electrical signal generated by the angle information unit to the analog calculating circuit only when the transducers of the second array are activated, whereby the first sweep signal and the second sweep signal are applied to the first deflection signal input and the second deflection signal input respectively when the transducers of the first array are activated whereas when the transducers of the second array are activated the signals that are applied to the first and second deflection signal inputs depend not only on the first and second sweep signals but also on the electrical signal generated by the angle information unit.

2. An apparatus as claimed in claim 1 wherein the angle information unit comprises a rotary potentiometer.

3. An apparatus as claimed in claim 1, wherein the analog calculating circuit comprises four 2-input multipliers, a sine-cosine converter and two adders, the inputs of the first multiplier being connected to the output of the first sweep generator and to the cosine output of the sine-cosine converter, respectively, the inputs of the second multiplier being connected to the output of the second sweep generator and to the sine output of the sine-cosine converter, respectively, the inputs of the third multiplier being connected to the output of the first sweep generator and to the sine output of the sine-cosine converter, respectively, and the inputs of the fourth multiplier being connected to the output of the second sweep generator and to the cosine output of the sine-cosine converter, the outputs of the first and the second multipliers being connected to the input of said first adder and the outputs of the third and the fourth multipliers being connected to the input of the said second adder.

4. An apparatus as claimed in claim 1, wherein the gate circuit comprises a field-effect transistor, the collector-emitter junction of which is connected between the angle information unit and the analog calculating circuit, and a flip-flop, the Q-output of which is connected to the gate of the field-effect transistor, the flip-flop being connected to be set when the first transducer in the second array is activated and reset when the first transducer in the first array is activated at the beginning of a scanning cycle.

* * * * *